(12) United States Patent
Toriumi

(10) Patent No.: US 12,022,833 B2
(45) Date of Patent: Jul. 2, 2024

(54) URACIL COMPOUND AND COMPOSITION FOR CONTROLLING HARMFUL ARTHROPODS COMPRISING THE SAME

(71) Applicant: Sumitomo Chemical Company, Limited, Tokyo (JP)

(72) Inventor: Tatsuya Toriumi, Takarazuka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 696 days.

(21) Appl. No.: 17/257,165

(22) PCT Filed: Jul. 4, 2019

(86) PCT No.: PCT/JP2019/026691
§ 371 (c)(1),
(2) Date: Dec. 30, 2020

(87) PCT Pub. No.: WO2020/009194
PCT Pub. Date: Jan. 9, 2020

(65) Prior Publication Data
US 2021/0176991 A1  Jun. 17, 2021

(30) Foreign Application Priority Data
Jul. 5, 2018  (JP) ................. 2018-128122

(51) Int. Cl.
*A01N 43/54* (2006.01)
*C07D 239/54* (2006.01)
*C07D 401/12* (2006.01)

(52) U.S. Cl.
CPC .......... *A01N 43/54* (2013.01); *C07D 401/12* (2013.01); *C07D 239/54* (2013.01)

(58) Field of Classification Search
CPC ................................................. C07D 239/54
See application file for complete search history.

(56) References Cited

U.S. PATENT DOCUMENTS

| | | | |
|---|---|---|---|
| 6,239,074 B1 | 5/2001 | Klintz et al. | |
| 7,109,148 B2 | 9/2006 | Mito | |
| 2001/0031865 A1 | 10/2001 | Klintz et al. | |
| 2004/0138063 A1 | 7/2004 | Mito | |

FOREIGN PATENT DOCUMENTS

| | | | |
|---|---|---|---|
| CA | 2034404 A1 | 7/1991 | |
| EP | 0438209 A1 | 7/1991 | |
| EP | 1122244 A1 | 8/2001 | |
| EP | 1422227 A1 | 5/2004 | |
| JP | H03287578 A | 12/1991 | |
| JP | H6510992 A | 12/1994 | |
| JP | 2001348376 A | 12/2001 | |
| JP | 2002155061 A | 5/2002 | |
| JP | 2002363010 A | * 12/2002 | |
| JP | 2003048885 A | 2/2003 | |
| WO | 2011137088 A1 | 11/2011 | |
| WO | 2017202768 A1 | 11/2017 | |

OTHER PUBLICATIONS

English Translation for JP 2002/363010 A (2002).*
Office Action issued Mar. 14, 2023 in JP Application No. 2020-529052.
1 Office Action issued Dec. 1, 2022 in CN Application No. 201980041158.4.
English Translation of International Preliminary Report on Patentability issued Jan. 5, 2021 in International Application No. PCT/JP2019/026691.
English Translation of International Search Report issued Oct. 1, 2019 in International Application No. PCT/JP2019/026691.
1 Examination Report issued Jul. 6, 2022 in IN Application No. 202047057414.
Examination Report issued Nov. 7, 2023 in AU Application No. 2019298549.

* cited by examiner

*Primary Examiner* — Kevin E Weddington
(74) *Attorney, Agent, or Firm* — Panitch Schwarze Belisario & Nadel LLP

(57) ABSTRACT

A compound represented by formula (A) has excellent control efficacy against a harmful arthropod.

(A)

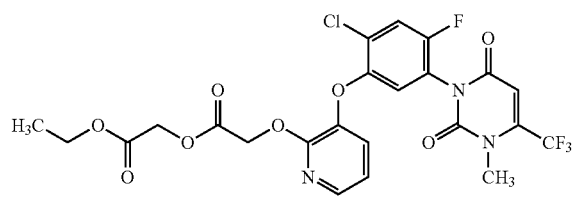

3 Claims, No Drawings

URACIL COMPOUND AND COMPOSITION FOR CONTROLLING HARMFUL ARTHROPODS COMPRISING THE SAME

CROSS-REFERENCE TO RELATED APPLICATIONS

This application is a Section 371 of International Application No. PCT/JP2019/026691, filed Jul. 4, 2019, which was published in the Japanese language on Jan. 9, 2020 under International Publication No. WO 2020/009194 A1, which claims priority under 35 U.S.C. § 119(b) to Japanese Application No. 2018-128122, filed on Jul. 5, 2018, the disclosures of which are incorporated herein by reference in their entireties.

TECHNICAL FIELD

The present invention relates to a uracil compound and a composition for controlling harmful arthropods.

BACKGROUND ART

To date, in order to control harmful arthropods, various compounds have been developed and come into practical use (see Non-Patent Document 1). Also, a compound represented by formula (B):

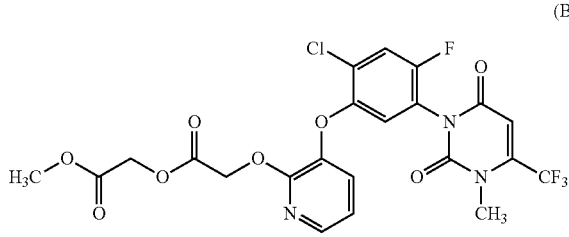

(B)

(hereinafter, referred to as "Compound B") is described as a withering agent (see Patent document 1).

CITATION LIST

Patent Document

Patent Document 1: U.S. Pat. No. 7,109,148 B2

Non-Patent Document

Non-Patent Document 1: The Pesticide Manual—17th edition (published by BCPC) ISBN 978-1-901396-88-1

SUMMARY OF THE INVENTION

Problems to be Solved by Invention

An object of the present invention is to provide a compound having excellent control effect against harmful arthropods.

Means to Solve Problems

The present inventor has intensively studied the above-mentioned problems, and found that a compound represented by the following formula (A) has some excellent efficacy on controlling harmful arthropods, which thus completed the present invention.

The present invention is as follows.

[1] A compound represented by formula (A):

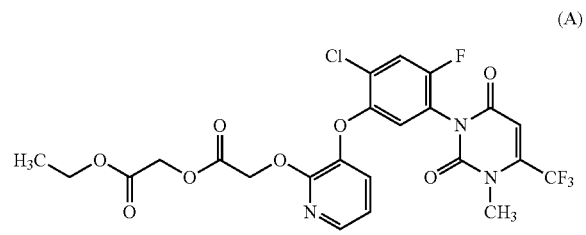 [SMILES: CCOC(=O)COC(=O)COc1ncccc1Oc1cc(-n2c(=O)cc(C(F)(F)F)n(C)c2=O)c(F)cc1Cl]

(A)

(hereinafter referred to as "Compound A").

[2] A composition comprising the compound according to the above [1] and an inert carrier (hereinafter, referred to as "Present composition" or "Composition of the present invention").

[3] A method for controlling a harmful arthropod which comprises applying an effective amount of the compound according to the above [1] to a harmful arthropod or a habitat where a harmful arthropod lives (hereinafter, referred to as "Present control method" or "Control method of the present invention").

Effect of Invention

The present invention can control harmful arthropods.

MODE FOR CARRYING OUT THE INVENTION

The composition of the present invention comprises the compound A and an inert carrier. The composition of the invention is usually prepared by mixing the compound A with the inert carrier such as a solid carrier and a liquid carrier and the like, and if necessary, adding a surfactant and other auxiliary agents for formulation to formulate into emulsifiable concentrates, oil solutions, powders, granules, wettable powders, water dispersible granules, flowables, dry flowables, microcapsules and the others.

The composition of the present invention usually comprises 0.0001 to 95% by weight of the compound A.

Examples of the solid carrier to be used in the formulation include fine powders or granules of clays (for example, kaolin clay, diatomaceous earth, bentonite, or acid white clay), dry silica, wet silica, talcs, ceramics, other inorganic minerals (for example, sericite, quartz, sulfur, active carbon, or calcium carbonate), or chemical fertilizers (for example, ammonium sulfate, ammonium phosphate, ammonium nitrate, urea, or ammonium chloride) and the others, as well as synthetic resins (for example, polyester resins such as polypropylene, polyacrylonitrile, polymethyl methacrylate or polyethylene terephthalate; nylon resins (for example, nylon-6, nylon-11 or nylon-66); polyamide resins; polyvinyl chloride, polyvinylidene chloride, vinyl chloride-propylene copolymers, and the others).

Examples of the liquid carriers include water; alcohols (for example, methanol or ethanol); ketones (for example, acetone or methyl ethyl ketone); aromatic hydrocarbons (for example, toluene or xylene); aliphatic hydrocarbons (for example, hexane or cyclohexane); esters (for example, ethyl acetate or butyl acetate); nitriles (for example, acetonitrile); ethers (for example, diisopropyl ether or diethyleneglycol dimethylether); amides (for example, N,N-dimethylformamide); sulfoxides (for example, dimethyl sulfoxide); and vegetable oils (for example, soybean oil or cottonseed oil).

Examples of the surfactants include nonionic surfactants such as polyoxyethylenated alkyl ethers, polyoxyethylenated alkyl aryl ether, and polyethylene glycol fatty acid ester; and anionic surfactants such as alkyl sulfonates, alkylbenzene sulfonates and alkyl sulfates.

Examples of the other auxiliary agents for formulation include, a binder, a dispersant, a colorant, and a stabilizer, and specific examples thereof include casein, gelatin, polysaccharides (for example, starch, gum arabic, cellulose derivatives, or alginic acid), lignin derivatives, bentonite, water-soluble synthetic polymers (for example, polyvinyl alcohol, polyvinyl pyrrolidone, polyacrylic acids or); acidic isopropyl phosphate, 2,6-di-tert-butyl-4-methylphenol, and BHA (a mixture of 2-tert-butyl-4-methoxyphenol and 3-tert-butyl-4-methoxyphenol).

Examples of the harmful arthropods on which the compound A has efficacies include the followings.

Hemiptera Pests:

Delphacidae (for example, *Laodelphax striatellus*, *Nilaparvata lugens*, *Sogatella furcifera*, *Peregrinus maidis*, *Javesella pellucida*, *Perkinsiella saccharicida*, or *Tagosodes orizicolus*);

Cicadellidae (for example, *Nephotettix cincticeps*, *Nephotettix virescens*, *Nephotettix nigropictus*, *Recilia dorsalis*, *Empoasca onukii*, *Empoasca fabae*, *Dalbulus maidis*, or *Cofana* spectra);

Cercopidae (for example, *Mahanarva posticata*, or *Mahanarva fimbriolata*);

Aphididae (for example, *Aphis fabae*, *Aphis glycines*, *Aphis gossypii*, *Aphis pomi*, *Aphis spiraecola*, *Myzus persicae*, *Brachycanclus helichrysi*, *Brevicoryne brassicae*, Rosy apple aphid (*Dysaphis plantaginea*), *Lipaphis erysimi*, *Macrosiphum euphorbiae*, *Aulacorthum solani*, *Nasonovia ribisnigri*, *Rhqpalosiphum padi*, *Rhqpalosiphum maidis*, *Toxoptera citricidus*, *Hyalopterus pruni*, *Melanaphis sacchari*, *Tetraneura nigriabdominalis*, *Ceratovacuna lanigera*, or *Eriosoma lanigerum*);

Phylloxeridae (for example, *Daktulosphaira vitifoliae*, Pecan *phylloxera* (*Phylloxera devastatrix*), Pecan leaf *phylloxera* (*Phylloxera notabilis*), or Southern pecan leaf *phylloxera* (*Phylloxera russellae*));

Adelgidae (for example, *Adelges tsugae*, *Adelges piceae*, or *Aphrastasia pectinatae*);

Pentatomidae (for example, *Scotinophara lurida*, Malayan rice black bug (*Scotinophara coarctata*), *Nezara antennata*, *Eysarcoris aeneus*, *Eysarcoris lewisi*, *Eysarcoris ventralis*, *Eysarcoris annamita*, *Halyomorpha halys*, *Nezara viridula*, Brown stink bug (*Euschistus heros*), Red banded stink bug (*Piezodorus guildinii*), *Oebalus pugnax*, *Dichelops melacanthus*);

Cydnidae (for example, Burrower brown bug (*Scaptocoris castanea*));

Alydidae (for example, *Riptortus pedestris*, *Leptocorisa chinensis*, or *Leptocorisa acuta*);

Coreidae (for example, *Cletus punctiger*, or *Leptoglossus australis*);

Lygaeidae (for example, *Caverelius saccharivorus*, *Togo hemipterus*, or *Blissus leucopterus*);

Miridae (for example, *Trigonotylus caelestialium*, *Stenotus rubrovittatus*, *Stenodema calcarata*, or *Lygus lineolaris*);

Aleyrodidae (for example, *Trialeurodes vaporariorum*, *Bemisia tabaci*, *Dialeurodes citri*, *Aleurocanthus spiniferus*, *Aleurocanthus camelliae*, or *Pealius euryae*);

Diaspididae (for example, *Abgrallaspis cyanophylli*, *Aonidiella aurantii*, *Diaspidiotus perniciosus*, *Pseudaulacaspis pentagona*, *Unaspis yanonensis*, or *Unaspis citri*);

Coccidae (for example, *Ceroplastes rubens*);

Margarodidae (for example, *Icerya purchasi*, or *Icerya seychellarum*);

Pseudococcidae (for example, *Phenacoccus solani*, *Phenacoccus solenopsis*, *Planococcus kraunhiae*, *Planococcus comstocki*, *Planococcus citri*, *Pseudococcus calceolariae*, *Pseudococcus longispinus*, or *Brevennia rehi*);

Psyllidae (for example, *Diaphorina citri*, *Trioza erytreae*, *Cacopsylla pyrisuga*, *Cacopsylla chinensis*, *Bactericera cockerelli*, or Pear psylla (*Cacopsylla pyricola*));

Tingidae (for example, *Corythucha ciliata*, *Corythucha marmorata*, *Stephanitis nashi*, or *Stephanitis pyrioides*);

Cimicidae (for example, *Cimex lectularius*);

Cicadidae (for example, Giant Cicada (*Quesada gigas*)); and

*Triatoma* spp. (for example, *Triatoma infestans*).

Lepidoptera

Crambidae (for example, *Chilo suppressalis*, Darkheaded stem borer (*Chilo polychrysus*), White stem borer (*Scirpophaga innotata*), *Scirpophaga incertulas*, *Rupela albina*, *Cnaphalocrocis medinalis*, *Marasmia patnalis*, *Marasmia exigua*, *Notarcha derogata*, *Ostrinia furnacalis*, European corn borer (*Ostrinia nubilalis*), *Hellula undalis*, *Herpetogramma luctuosale*, *Pediasia teterrellus*, *Nymphula depunctalis*, or Sugarcane borer (*Diatraea saccharalis*));

Pyralidae (for example, *Elasmopalpus lignosellus*, *Plodia interpunctella*, or *Euzophera batangensis*);

Noctuidae (for example, *Spodoptera litura*, *Spodoptera exigua*, *Mythimna separata*, *Mamestra brassicae*, *Sesamia inferens*, *Spodoptera mauritia*, *Naranga aenescens*, *Spodoptera frugiperda*, *Spodoptera exempta*, *Agrotis Ipsilon*, *Autographa nigrisigna*, *Plusia festucae*, Soybean looper (*Chrysodeixis includens*), *Trichoplusia* spp., *Heliothis* spp. (for example, *Heliothis virescens*), *Helicoverpa* spp. (for example, *Helicoverpa armigera*, or *Helicoverpa zea*), Velvetbean caterpillar (*Anticarsia gemmatalis*), Cotton leafworm (*Alabama argillacea*), or Hop vine borer (*Hydraecia immanis*)), Pieridae (for example, *Pieris rapae*);

Tortricidae (for example, *Grapholita molesta*, *Grapholita dimorpha*, *Leguminivora glycinivorella*, *Matsumuraeses azukivora*, *Adoxophyes orana fasciata*, *Adoxophyes honmai*, *Homona magnanima*, *Archips fuscocupreanus*, *Cydia pomonella*, *Tetramoera schistaceana*, Bean Shoot Borer (*Epinotia aporema*), or Citrus fruit borer (*Ecdytolopha aurantiana*));

Gracillariidae (for example, *Caloptilia theivora*, or *Phyllonorycter ringoniella*);

Carposinidae (for example, *Carposina sasakii*);

Lyonetiidae (for example, Coffee Leaf miner (*Leucoptera coffeela*), *Lyonetia clerkella*, or *Lyonetia prunifoliella*);

Lymantriidae (for example, *Lymantria* spp. (for example, *Lymantria dispar*), or *Euproctis* spp. (for example, *Euproctis pseudoconspersa*));

Pluteliidae (for example, *Plutella xylostella*);

Gelechiidae (for example, *Anarsia lineatella*, *Helcystogramma triannulellum*, *Pectinophora gossypiella*, *Phthorimaea operculella*, or *Tuta absolut*);

Arctiidae (for example, *Hyphantria cunea*);

Castniidae (for example, Giant Sugarcane borer (*Telchin licus*));

Cossidae (for example, *Cosus insularis*);

Geometridae (for example, *Ascotis selenaria*);

Limacodidae (for example, *Parasa lepida*);

Stathmopodidae (for example, *Stathmopoda masinissa*);

Sphingidae (for example, *Acherontia lachesis*);

Sesiidae (for example, *Nokona feralis, Synanthedon hector,* or *Synanthedon tenuis*);

Hesperiidae (for example, *Parnara guttata*); and

Tinedae (for example, *Tinea translucens* or *Tineola bisselliella*).

Thysanoptera

Thripidae (for example, *Frankliniella occidentalis, Thrips palmi, Scirtothrips dorsalis, Thrips tabaci, Frankliniella intonsa, Stenchaetothrips biformis,* or *Echinothrips americanus*); and Phlaeothripidae (for example, *Haplothrips aculeatus*).

The method for controlling harmful arthropods of the present invention comprises applying an effective amount of the compound A to harmful arthropods directly, and/or to a habitat where a harmful arthropod lives (for example, plant or soil).

An application dose of the compound A is usually within a range of 1 to 10,000 g per 10,000 m². When the compound A is formulated into emulsifiable concentrates, wettable powders, flowables, and the others, such formulations are usually applied after diluting it with water in such a way that a concentration of the active ingredient is within a range of 0.01 to 10,000 ppm, and in the case of being formulated into dust formulations, granules, and the others, such formulations are used as itself.

Also, the composition of the present invention may be used as an agent for controlling harmful arthropods in agricultural lands such as fields, paddy fields, turfs, and orchards.

EXAMPLES

Hereinafter, the present invention is explained in more detail by using Preparation Example, and Test Example and the like, however, the present invention should not be limited to these examples. The Preparation Examples of the compound A is shown below.

Preparation Example

To a mixture of 2.00 g of (3-{2-Chloro-4-fluoro-5-[3-methyl-2,6-dioxo-4-(trifluoromethyl)-1,2,3,6-tetrahydropyrimidin-1-yl]phenoxyl-2-pyridiloxy} acetic acid, which was prepared by the method described in the U.S. Pat. No. 6,537,948 B2 specification, 8.01 g of xylene and 0.05 g of boron trifluoride diethylether complex was added dropwise 1.61 g of a solution containing 40% ethyl diazoacetate in xylene at 50° C., and the mixture was then stirred for 4 hours. To the resulting mixture were further added 0.05 g of boron trifluoride diethylether complex and 1.94 g of a solution containing 40% ethyl diazoacetate in xylene, and the mixture was then stirred at 50° C. for 1 hour. The resulting mixture was allowed to cool to room temperature, and 10% aqueous sulfuric acid solution was then added, and the mixture was extracted with ethyl acetate. The resulting organic layer was washed with saturated aqueous sodium bicarbonate solution, and concentrated under reduced pressure. The resulting residue was subjected to a silica gel chromatography to obtain 1.01 g of the compound A.

¹H-NMR data of the compound A is shown below.

¹H-NMR (CDCl₃) δ (ppm): 7.94-7.92 (1H, m), 7.37 (1H, d, J=9.1 Hz), 7.33-7.30 (1H, m), 6.96-6.91 (1H, m), 6.89 (1H, d, J=6.6 Hz), 6.29 (1H, s), 5.12-4.99 (2H, m), 4.63 (2H, s), 4.20 (2H, q, J=7.1 Hz), 3.51 (3H, s), 1.27 (3H, t, J=7.1 Hz).

Next, Test Examples are used to show an efficacy of the compound A on controlling harmful arthropods. Herein, the term "part(s)" means "part(s) by weight".

Test Example 1

Thirty-five (35) parts of a mixture of polyoxyethylene alkyl ether sulfate ammonium salt and wet silica (weight ratio of 1:1), 20 parts of the compound A, and 45 parts of water were mixed thoroughly. The resulting mixture was diluted with water containing 0.03 v/v % of Shindain (registered trademark) to prepare a diluted solution containing 500 ppm of the compound A. The diluted solution was sprayed into the cabbage (*Brassicae oleracea*) seedling (on the developmental stage of the second to third true leaf) that is planted in a container in a ratio of 20 mL/seedling.

Thereafter, the stem and leaf of thereof was cut out and then was installed into the container that was covered with the filter paper. Five second instar larvae of diamondback moth (*Plutella xylostella*) were released into the container, and the container was allowed to stand at 25° C. for 5 days. Thereafter, the surviving insects were counted, and the mortality was calculated from the following equation, and as a result, the mortality was 100%.

Mortality (%)=(1−Number of the surviving insects/5)×100

Comparative Test Example 1

The test was carried out according to Test Example 1 using the compound B instead of the compound A. As a result, the mortality was 0%.

INDUSTRIAL APPLICABILITY

The compound A shows an excellent control effect against harmful arthropods.

The invention claimed is:

1. A compound represented by formula (A):

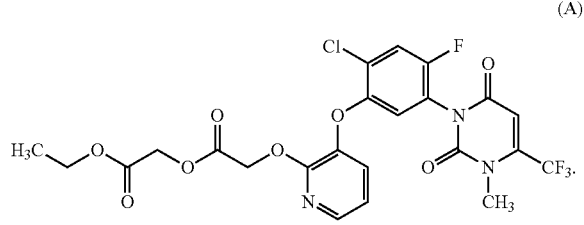 [SMILES: CCOC(=O)COC(=O)COc1ncccc1Oc1cc(-n2c(=O)cc(C(F)(F)F)n(C)c2=O)c(F)cc1Cl]

(A)

2. A composition comprising the compound according to claim 1 and an inert carrier.

3. A method for controlling a harmful arthropod which comprises applying an effective amount of the compound according to claim 1 to a harmful arthropod or a habitat where a harmful arthropod lives.

* * * * *